US009675439B2

(12) United States Patent
Havel et al.

(10) Patent No.: US 9,675,439 B2
(45) Date of Patent: Jun. 13, 2017

(54) STENT DESIGNS FOR REDUCED INFOLDING OF GRAFT MATERIAL

(71) Applicant: Cook Medical Technologies LLC, Bloomington, IN (US)

(72) Inventors: William J. Havel, West Lafayette, IN (US); Matthew S. Huser, West Lafayette, IN (US); Jarin Kratzberg, Lafayette, IN (US); Shuo Yang, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 560 days.

(21) Appl. No.: 14/105,979

(22) Filed: Dec. 13, 2013

(65) Prior Publication Data
US 2014/0180390 A1 Jun. 26, 2014

Related U.S. Application Data

(60) Provisional application No. 61/745,159, filed on Dec. 21, 2012.

(51) Int. Cl.
A61F 2/91 (2013.01)
A61F 2/07 (2013.01)
A61F 2/848 (2013.01)

(52) U.S. Cl.
CPC .................. A61F 2/07 (2013.01); A61F 2/91 (2013.01); A61F 2002/075 (2013.01);
(Continued)

(58) Field of Classification Search
CPC ........ A61F 2002/075; A61F 2002/8483; A61F 2002/077; A61F 2002/072; A61F 2/07; A61F 2/91
(Continued)

(56) References Cited

U.S. PATENT DOCUMENTS 5,562,724 A 10/1996 Vorwerk et al.
5,720,776 A 2/1998 Chuter et al.
(Continued)

FOREIGN PATENT DOCUMENTS

WO WO 2005/032403 A2 4/2005
WO WO 2009/085190 A1 7/2009
(Continued)

OTHER PUBLICATIONS

Extended European Search in related application No. 13275316.1-1651/2745806 (7 pgs).

Primary Examiner — Kathleen Holwerda
Assistant Examiner — Socrates L Boutsikaris
(74) Attorney, Agent, or Firm — Brinks Gilson & Lione

(57) ABSTRACT

A stent-graft comprises a substantially tubular graft material, and a stent coupled to the graft material. The stent has proximal and distal ends and further has compressed and deployed states. The proximal end is disposed proximally beyond a proximal edge of the graft material, and the distal end has at least one portion overlapping with the proximal edge of the graft material. In one example, the stent comprises at least one distal apex having a bifurcation extending into first and second leg regions. A distal end of the first leg region is positioned to overlap the graft material at a location circumferentially spaced apart from a location at which a distal end of the second leg region overlaps the graft material in the deployed state.

17 Claims, 4 Drawing Sheets

(52) U.S. Cl.
CPC ............... *A61F 2002/8483* (2013.01); *A61F 2220/0075* (2013.01); *A61F 2250/0063* (2013.01)

(58) Field of Classification Search
USPC .......... 623/1.11, 1.12, 1.13, 1.15, 1.16, 1.23
See application file for complete search history.

(56) References Cited

U.S. PATENT DOCUMENTS

| | | | |
|---|---|---|---|
| 6,004,347 | A | 12/1999 | McNamara et al. |
| 6,099,558 | A | 8/2000 | White et al. |
| 6,102,940 | A | 8/2000 | Robichon et al. |
| 6,123,722 | A | 9/2000 | Fogarty et al. |
| 6,368,345 | B1 | 4/2002 | Dehdashtian et al. |
| 6,652,580 | B1 | 11/2003 | Chuter et al. |
| 7,147,660 | B2 | 12/2006 | Chobotov et al. |
| 7,175,652 | B2 | 2/2007 | Cook et al. |
| 7,226,474 | B2 | 6/2007 | Iancea et al. |
| 7,615,072 | B2 | 11/2009 | Rust et al. |
| 7,637,932 | B2 | 12/2009 | Bolduc et al. |
| 7,655,034 | B2 | 2/2010 | Mitchell et al. |
| 7,666,221 | B2 | 2/2010 | Escano |
| 7,708,771 | B2 | 5/2010 | Chuter et al. |
| 7,763,063 | B2 | 7/2010 | Arbefeuille et al. |
| 7,942,924 | B1 | 5/2011 | Perez et al. |
| 2004/0015229 | A1* | 1/2004 | Fulkerson ............... A61F 2/91 623/1.22 |
| 2006/0195172 | A1 | 8/2006 | Luo et al. |
| 2007/0055345 | A1 | 3/2007 | Arbefeuille |
| 2007/0219620 | A1 | 9/2007 | Eells et al. |
| 2007/0239267 | A1 | 10/2007 | Hendricks et al. |
| 2008/0114441 | A1* | 5/2008 | Rust ..................... A61F 2/07 623/1.13 |
| 2008/0208312 | A1 | 8/2008 | Kwitkin et al. |
| 2009/0204202 | A1 | 8/2009 | Dierking et al. |
| 2010/0161028 | A1 | 6/2010 | Chuter et al. |
| 2010/0286757 | A1 | 11/2010 | Petersen et al. |
| 2011/0202122 | A1* | 8/2011 | Takeuchi ............... A61F 2/91 623/1.2 |

FOREIGN PATENT DOCUMENTS

| | | |
|---|---|---|
| WO | WO2011/031981 | 3/2011 |
| WO | WO 2011/107243 A1 | 9/2011 |

* cited by examiner

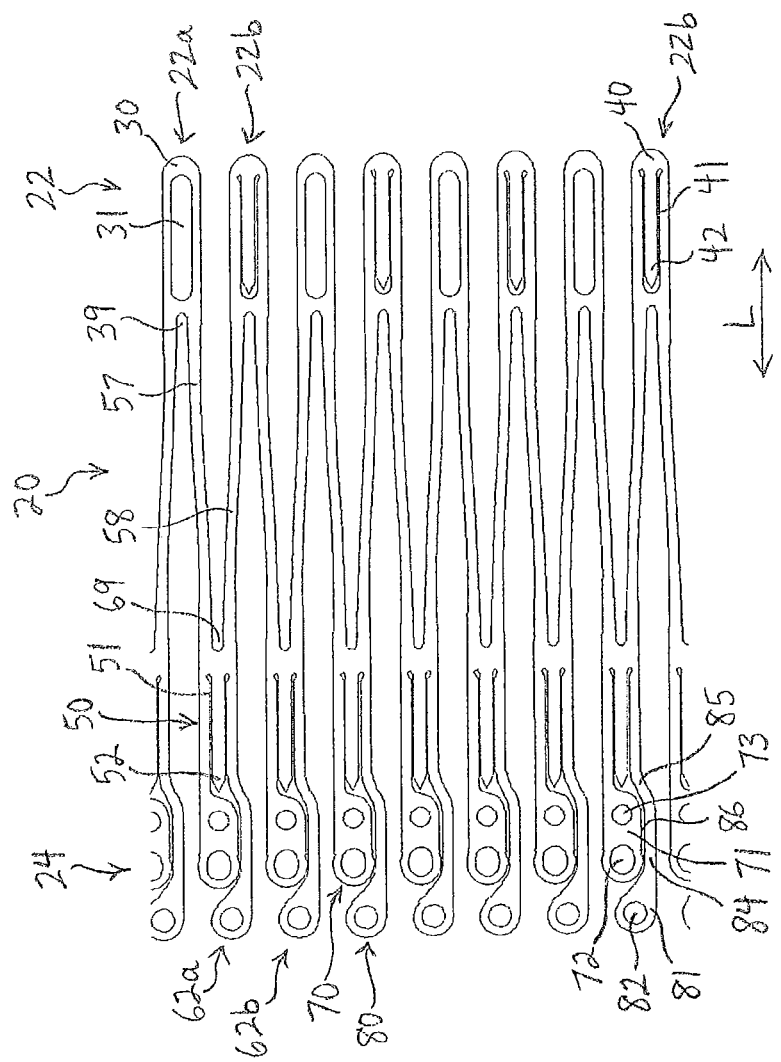

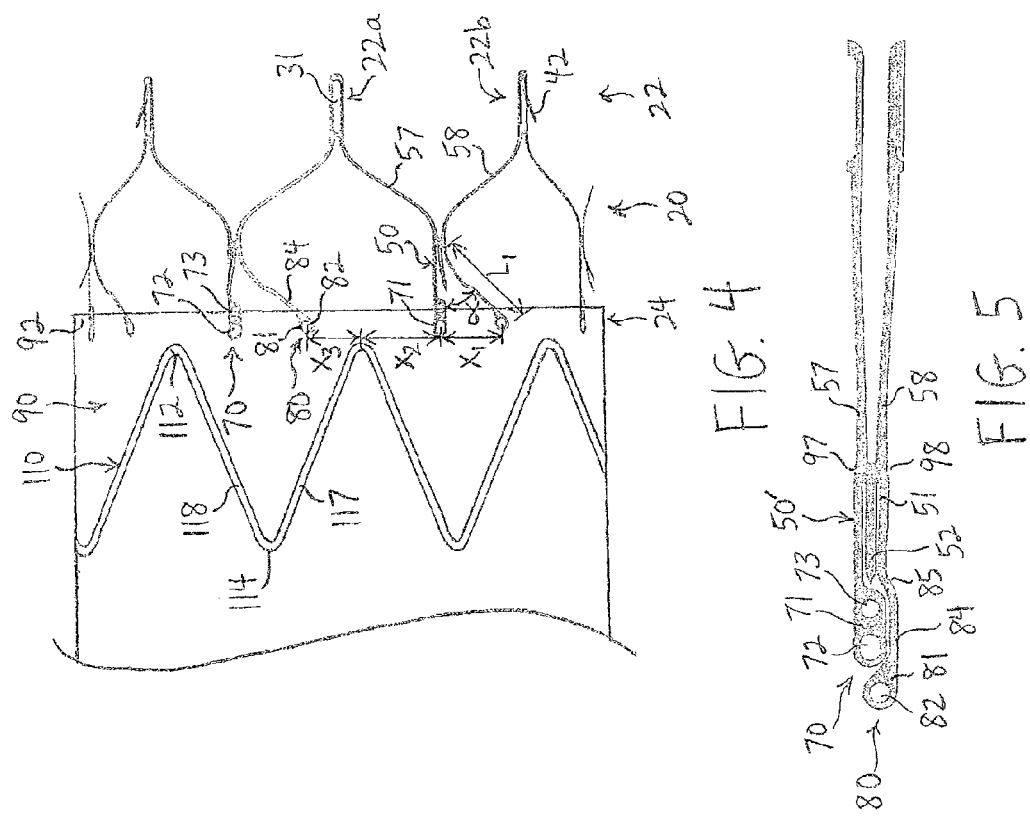

STENT DESIGNS FOR REDUCED INFOLDING OF GRAFT MATERIAL

PRIORITY CLAIM

This invention claims the benefit of priority of U.S. Provisional Application Ser. No. 61/745,159, entitled "Stent Designs for Reduced Infolding of Graft Material," filed Dec. 21, 2012, the disclosure of which is hereby incorporated by reference in its entirety.

BACKGROUND

The present embodiments relate generally to apparatus and methods for treating medical conditions, and more specifically, to stents and stent-grafts for use in body vessels to treat those medical conditions.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents may be used a part of a "stent-graft," whereby one or more stents are placed in or about a graft and used to hold the graft in an open configuration to treat an aneurysm or other condition. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When a stent-graft having at least one stent is deployed in a vessel, such as the aorta, and blood flows in a proximal to distal direction away from the heart, there is a possibility of "infolding" of graft material, particularly at the proximal end of the graft material. For example, if a stent-graft is deployed to treat an abdominal aortic aneurysm, blood flowing distally into the graft may pull the proximal edge of the graft in a radially inward direction, particularly if an optimal proximal seal is not achieved with the vessel wall. In this case, the graft material that becomes pulled inward may impede blood flow through the stent-graft lumen, or an endoleak may occur. Furthermore, if the proximal end of a stent-graft is deployed in a curved portion of a vessel, such as the aortic arch or thoracic aorta, it may be to difficult to conform the proximal edge of the stent-graft to the curving vessel wall, which also may result in blood flow catching on the graft and potential endoleaks.

SUMMARY

A stent-graft comprises a substantially tubular graft material, and a stent coupled to the graft material. The stent has proximal and distal ends and further has compressed and deployed states. The proximal end is disposed proximally beyond a proximal edge of the graft material, and the distal end has at least one portion overlapping with the proximal edge of the graft material.

In one example, the stent comprises at least one distal apex having a bifurcation extending into first and second leg regions. A distal end of the first leg region is positioned to overlap with the graft material at a location circumferentially spaced apart from a location at which a distal end of the second leg region overlaps with the graft material in the deployed state. In one embodiment, the first leg region may be generally parallel to a longitudinal axis of the stent in both the compressed and deployed states, while the second leg region may be parallel to the longitudinal axis in the compressed state but angled relative to the longitudinal axis in the deployed state.

The graft material may be secured to the stent at suture bores of the first and second leg regions. The suture bore of the second leg region may be positioned distally of the suture bore of the first leg region in the compressed state. The suture bore of the second leg region may move in a distal to proximal direction during deployment, such that it is approximately even with an axial position of the suture bore of the first leg region in the deployed state. The first leg region further may comprise an imaging bore disposed proximal to the suture bore of the first leg region, the imaging bore being disposed at the location corresponding to an endpoint of the proximal edge of the graft material.

A second stent may be provided at a location overlapping the graft material. The second stent may comprise a proximal apex that is positioned circumferentially between the distal ends of the first and second leg regions in the deployed state.

In an alternative embodiment, a stent may comprise a generally zig-zag shape formed from a wire comprising a series of proximal apices, a series of distal apices, and a plurality of first and second strut segments disposed between the series of proximal apices and the series of distal apices. The proximal apices may be disposed proximally beyond a proximal edge of the graft material, and the distal apices may at least partially overlap with the graft material. An extension region extends from at least one of the strut segments. The extension region comprises a proximal end that is secured to the strut segment at a location between the proximal and distal apices. Further, the extension region comprises a distal end that is circumferentially spaced apart from an adjacent distal apex in the deployed state.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 2 is a side view of the stent of FIG. 1 in a compressed state, depicted as flattened for illustrative purposes.

FIG. 3 is a side view depicting features of a distal apex of the stent of FIG. 1

FIG. 4 is a side view of the stent of FIGS. 1-3 being coupled to a graft to form a stent-graft.

FIG. 5 is a side view depicting an alternative segment of the stent of FIGS. 1-4.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Referring to FIGS. 1-4, a stent 20 according to a first embodiment may be manufactured from a continuous cylinder into which a pattern may be cut by a laser or by chemical etching to produce slits in the wall of the cylinder. The resulting structure may thereafter be heat set to give it a desired final configuration. The preferred final configuration includes a shape having a series of proximal apices and a series of distal apices.

The stent 20 has a reduced diameter delivery state so that it may be advanced to a target location within a vessel or duct. The stent 20 also has an expanded deployed state to apply a radially outward force upon at least a portion of a vessel or duct, e.g., to maintain patency within a passageway, or to hold open the lumen of a graft. In the expanded state, fluid flow is allowed through a central lumen of the stent 20.

The stent 20 may be manufactured from a super-elastic material. Solely by way of example, the super-elastic material may comprise a shape-memory alloy, such as a nickel titanium alloy (nitinol). If the stent 20 comprises a self-expanding material such as nitinol, the stent may be heat-set into the desired expanded state, whereby the stent 20 can assume a relaxed configuration in which it assumes the preconfigured first expanded inner diameter upon application of a certain cold or hot medium. Alternatively, the stent 20 may be made from other metals and alloys that allow the stent 20 to return to its original, expanded configuration upon deployment, without inducing a permanent strain on the material due to compression. Solely by way of example, the stent 20 may comprise other materials such as stainless steel, cobalt-chrome alloys, amorphous metals, tantalum, platinum, gold and titanium. The stent 20 also may be made from non-metallic materials, such as thermoplastics and other polymers.

Figure 1:
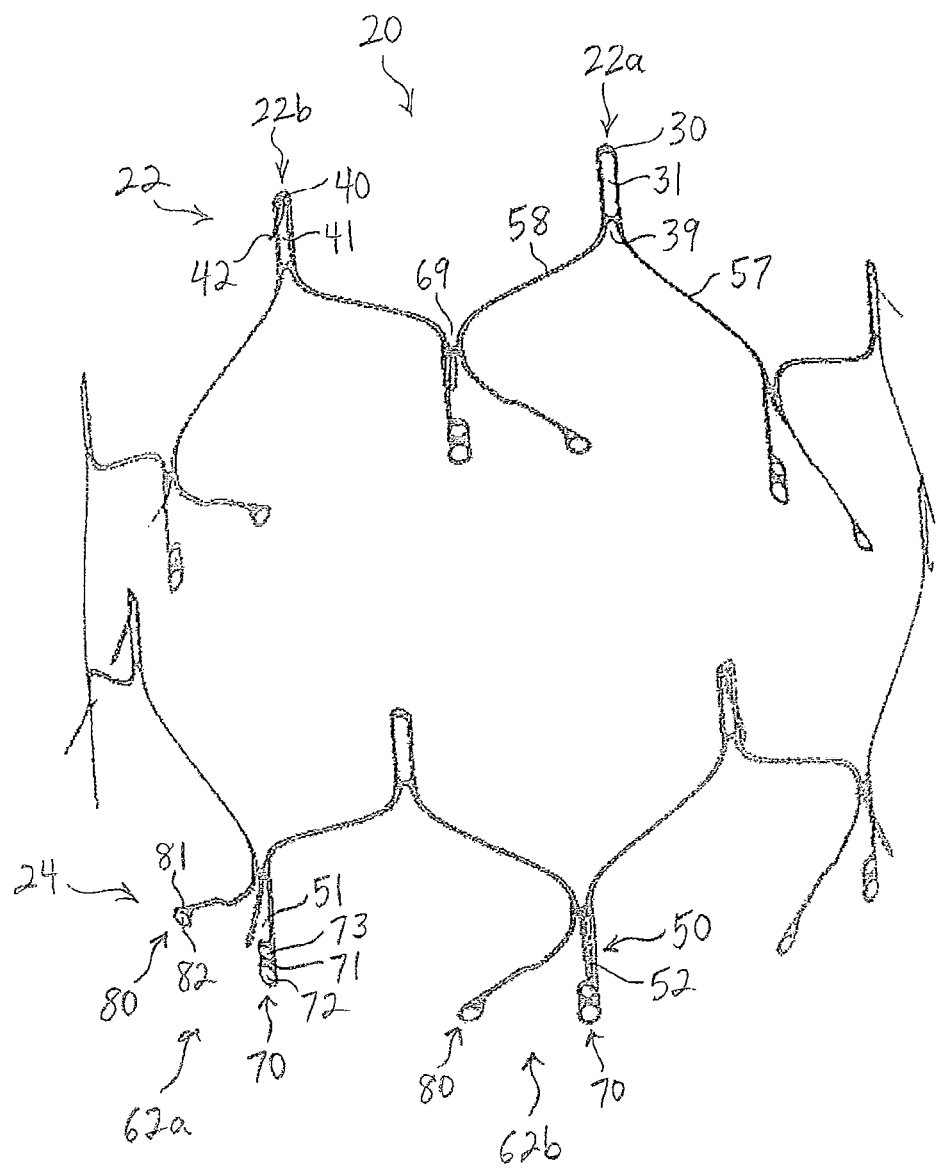
FIG. 1 is an elevated perspective view of a stent in accordance with one embodiment in a cylindrical, deployed state.

A proximal end 22 of the stent 20 comprises multiple adjacent proximal apices 22a and 22b, while a distal end 24 of the stent 20 comprises multiple adjacent distal apices 62a and 62b, as shown in FIGS. 1-2. One or more pairs of adjacent, proximal apices 22a and 22b may comprise different features. For example, a first proximal apex 22a may comprise an end region 30 having a bore 31 formed therein, where the bore 31 is configured to receive a trigger wire. A second, adjacent proximal apex 22b comprises an end region 40 having an integral barb 42 formed therein, as best seen in FIGS. 1-2.

The stent 20 may be delivered to a target site in a compressed state using a plurality of trigger wires. A single trigger wire may be looped through the bore 31 of each first proximal apex 22a to restrain the stent 20 during delivery. Trigger wires are not coupled to the second proximal apices 22b, which comprise the barbs 42. By restraining selected ones of the proximal apices, such as each first proximal apex 22a, the adjacent second proximal apices 22b also may be indirectly pulled in a radially inward direction during delivery. The configuration of the stent 20, and in particular angled segments 57 and 58 described below, facilitates the indirect compression of the adjacent second proximal apices 22b. Advantageously, since only selected ones of the proximal apices are restrained during delivery, the number of trigger wires may be reduced.

The barbs 42 may be formed by laser cutting a desired barb shape into the end regions 40. A slit 41 therefore is formed into each end region 40 after the desired barb shape is formed, as best seen in FIG. 2. Once the desired barb shape is cut, a main body of the barb 42 may be bent in a radially outward direction with respect to the end region 40. The angle may comprise any acute angle, or alternatively may be substantially orthogonal or obtuse. If desired, the barbs 42 may be sharpened, for example, by grinding the tip of the barb, to facilitate engagement at a target tissue site.

In one configuration, the proximal and distal apices are not directly aligned with one another. For example, as shown in FIGS. 1-2 and FIG. 4, a first angled segment 57 may be disposed between a proximal apex 22a and a corresponding distal apex 62a, and a second angled segment 58 may be disposed between the same proximal apex 22a and an adjacent distal apex 62b. In effect, each proximal apex 22a and 22b extends distally and splits into the first and second angled strut segments 57 and 58, respectively, thereby forming a proximal vertex 39. Similarly, each distal apex 62a and 62b extends proximally and splits into the first and second angled strut segments 57 and 58, respectively, thereby forming a distal vertex 69. In this manner, the stent 20 may be formed into a continuous, generally cylindrical shape, as shown in FIG. 1.

Expansion of the stent 20 is at least partly provided by the angled strut segments 57 and 58, which may be substantially parallel to one another in the compressed state shown in FIG. 2, but tend to bow outward away from one another in the expanded state shown in FIG. 1 and FIG. 4. In the compressed state, the first and second angled strut segments 57 and 58 may be compressed such that they are substantially parallel to one another along a longitudinal axis L of the stent 20, as shown in FIG. 2. In the expanded state shown in FIG. 1 and FIG. 4, the first and second angled strut segments 57 and 58 may be disposed at an angle of about 20-60 degrees relative to the longitudinal axis L.

The first and second angled strut segments 57 and 58 meet with one another distally to form a distal transition region 50. Each distal transition region 50 may be oriented in a direction that is substantially parallel to the longitudinal axis L of the stent 20, as shown in FIG. 2. Further, each distal transition region 50 may comprise a larger surface area relative to the individual segments, since the distal transition region 50 is composed substantially of multiple different angled segments 57 and 58 meeting up together. At least one barb 52 may be formed integrally by laser cutting a desired barb shape, thereby forming a slit 51 into the distal transition region 50, as best seen in FIG. 2. Since the distal transition regions 50 may comprise an increased surface area relative to other regions of the stent 20, it may be easier to perforate portions of the distal transition region 50 without adversely affecting the structural integrity of the stent.

The distal transition regions 50 begin to form the distal apices 62a and 62b. In this embodiment, first and second leg regions 70 and 80 extend distally from a distal transition region 50 in a bifurcated manner, as shown in FIGS. 1-4, thereby forming one of the distal apices 62a or 62b of the stent 20. In one embodiment, a first angled strut segments 57 is generally parallel and continuous through the distal transition region 50 with a first leg region 70 in a compressed state, while a second angled strut segments 58 is generally parallel and continuous through the distal transition region 50 with a second leg region 80 in the compressed state, as best seen in FIG. 2.

Each of the first leg regions 70 comprises a body portion 71 having a suture bore 72 and an imaging bore 73 formed therein, as shown seen in FIGS. 1-4. The first leg regions 70 may be coupled to a proximal edge 92 of graft material 90, as depicted in FIG. 4, using one or more sutures that are looped through the graft material 90 and the bores 72 of the stent 20. In this manner, the stent 20 may be used as an attachment stent for endovascular graft fixation. For example, the graft material 90 may overlap with an aneurysm to seal off fluid flow into the aneurysm, while the proximal end 22 of the stent 20 may extend in a proximal direction away from the graft material 90, e.g., to engage a healthy portion of a vessel wall away from a diseased portion of the aneurysm.

The imaging bore 73 of the first leg region 70 may be disposed between the suture bore 72 and the barb 52, as seen in FIGS. 1-4. The imaging bore 73 may receive any suitable radiopaque marker, such as a gold marker. Preferably, the imaging bores 73 and associated radiopaque markers are provided on each distal apex 62a and 62b. Alternatively, the imaging bores 73 may be disposed on alternating distal apices 62a and 62b, or disposed on every third or fourth apex around the perimeter of the stent. The imaging bores 73 may be beveled, or alternatively, may be substantially orthogonal to the strut of the first leg regions 70.

In use, the imaging bores 73 may be aligned with the proximal edge 92 of the graft material 90, as depicted in FIG. 4, in a manner that is particularly well-suited when the stent 20 is used for endovascular graft fixation. More specifically, the suture bore 72 overlaps with a proximal region of the graft material 90, thereby allowing a suture to couple the stent 20 to the graft material 90 with some desired degree of overlap. The proximal edge 92 of the graft material 90 therefore may be aligned precisely with the imaging bores 73, as shown in FIG. 4. Advantageously, a physician may know exactly where the proximal edge 92 of the graft material 90 is being placed because he or she can view the position of the radiopaque markers in the imaging bores 73. Therefore, the chances of inadvertently overlapping the graft material with a branch vessel, or another undesired location, may be reduced.

Each of the second leg regions 80 comprises a body portion 81 having a suture bore 82 formed therein. The second leg regions 80 also are coupled to the proximal end 92 of the graft material 90, as shown in FIG. 4, using one or more sutures that are looped through the graft material 90 and the suture bores 82.

In the compressed state, the suture bores 82 of the second leg regions 80 are disposed distal to the suture bores 72 of the first leg regions 70, as shown in FIG. 2. The second leg regions 80 may comprise an extension region 84, which extends along an axial length and around an outer perimeter of the body portion 71, as shown in FIG. 2. In this manner, the extension region 84 serves as a strut extension in the compressed state to achieve an axial offset between the body portion 81 having the suture bore 82 of the second leg region 80, and the body portion 71 having the suture bore 72 of the first leg region 70.

The provision of an axial offset between the body portions 71 and 81, each of which have widths that must accommodate their respective bores, reduces the delivery profile of the stent 20 because material overlap at axial positions is reduced. It should be noted that the extension region 84 has a narrower width relative to the body portions 71 and 81, in order to achieve a further reduction in delivery profile.

In the compressed state depicted in FIG. 2, a tapered strut region 85 is provided between a strut of the distal transition region 50 and the extension region 84 of the second leg region 80. The tapered strut region 85 maneuvers the extension region 84 to a position circumferentially around the body portion 71 of the first leg region 70. This structure forms a recessed portion 86 within the extension region 84 at locations between the distal transition region 50 and the body portion 81 of the second leg region 80. The body portion 71 of the first leg region 70 is at least partially nested within the recessed portion 86 in the compressed state.

In a deployed state, shown in FIG. 1 and FIGS. 3-4, the extension region 84 of the second leg region 80 is disposed at an angle $\alpha$ relative to the distal transition region 50 and the body portion 71 of the first leg region 70, as depicted in FIG. 4. In one example, the angle $\alpha$ may be between about 15 degrees and about 75 degrees. During deployment, the body region 81 comprising the suture bore 82 also moves in a distal to proximal direction, relative to the body region 71, as best seen in FIG. 3. In this manner, the suture bore 72 of the body region 71 may be disposed at approximately the same axial position in the deployed state relative to the suture bore 82 of the body region 81, as shown in FIG. 3. When used in conjunction with the graft material 90, the result is that both the suture bore 72 of the body region 71 and the suture bore 82 of the body region 81 are disposed at approximately the same axial position, slightly distal to the proximal edge 92 of the graft material 90, as shown in FIG. 4.

The second leg region 80 may be heat-set into the desired deployed state, according to the techniques described above, to thereby achieve the expanded state shown in FIG. 1 and FIGS. 3-4 upon deployment of the distal end 24 of the stent 20. It should be noted that, in the deployed state, the first leg region 70 generally provides longitudinal strength necessary for the stent 20, while the second leg region 80 does not carry a significant longitudinal load, but assists in significantly reducing infolding of the graft material 90.

Advantageously, by providing a bifurcated distal apex having leg regions 70 and 80 with circumferentially spaced-apart body regions 71 and 81, infolding at the proximal edge 92 of the graft material 90 may be reduced. In particular, it is expected that the likelihood of infolding may be reduced by about 50% by use of the stent 20 alone, since each distal apex 62a and 62b provides two separate and distinct leg regions 70 and 80 that can reduce infolding, as compared to the provision of just one region of a conventional distal apex being secured to the graft material 90.

In the deployed state, a circumferential spacing $x_1$, depicted in FIG. 4, is provided between the body region 71 of the first leg region 70 and the body region 81 of the second leg region 80. The combination of the angle $\alpha$, together with a distance $L_1$ that comprises the length of the extension region 84 and the body region 81, affects the degree of the circumferential spacing $x_1$ between the body region 71 of the first leg region 70 relative to the body region 81 of the second leg region 80. The degree of circumferential spacing $x_1$, and accordingly the angle α, together with a distance $L_1$, may be selected based on the particular needs of a procedure. In one non-limiting example, one particular body region 81 may be positioned approximately halfway circumferentially in-between surrounding body regions 71. In the exemplary depiction of FIGS. 1-4, in which eight distal apices are provided, then each of the body regions 71 may be positioned about 45 degrees apart from one another around the circumference of the stent 20, and the degree of circumferential spacing $x_1$ between body regions 71 and 81 will be about 22.5 degrees. Such dimensions may be varied. For example, if 100% is the total distance between two adjacent body regions 71 in the deployed state, then one particular body region 81 may be anywhere from about 5% to about 50% of the distance from its nearest adjacent body region 71.

The amount of separation between the bifurcated leg regions 70 and 80 of each distal apex may further be selected based on the structure of the nearby stent-graft, e.g., taking into account structures of different stents that are positioned along the graft material 90. In the embodiment of FIG. 4, a second stent 110 is provided and may comprise a generally zig-zag shape formed from a single wire comprising a series of proximal apices 112 disposed at the proximal end of the second stent 110, a series of distal apices 114 disposed at the distal end of the second stent 110, and a plurality of strut segments 117 and 118 disposed between the series of proximal apices 112 and the series of distal apices 114, as shown in FIG. 4. The second stent 110 overlaps with the graft material 90 along a longitudinal length between the proximal and distal ends of the second stent 110, such that the series of proximal apices 112 of the second stent 110 are each disposed distal to the proximal edge 92 of the graft material 90, as shown in FIG. 4. When such a second stent 110 is used, the proximal apices 112 may be positioned approximately halfway circumferentially in-between surrounding body regions 71 and 81. In the examples shown herein, in which eight distal apices of the stent 20 are provided, in addition to eight proximal apices of the second stent 110, then a degree of circumferential spacing $x_2$ between the one proximal apex 112 and its nearest adjacent body region 71 will be about 15 degrees, and another circumferential spacing $x_3$ between the same proximal apex 112 and its nearest adjacent body region 81 will also be about 15 degrees, as depicted in FIG. 4.

In the example of FIG. 4, there will be 24 total different regions that are capable of preventing infolding at the proximal edge 92 of the graft material 90. Specifically, there are eight body regions 71 of the first leg regions 70, eight body regions 81 of the second leg regions 80, and eight proximal apices 112 of the second stent, accounting for 24 contact points in the vicinity of the proximal edge 92 of the graft material 90. The circumferential spacings $x_1$, $x_2$ and $x_3$ between these 24 components need not be exactly 15 degrees each, i.e., equidistant around the circumference, but each of these 24 different components preferably are spaced apart in the range of about 10-20 degrees apart from one another in the example in which 24 total different regions that are capable of preventing infolding are provided. Advantageously, there is expected to be a significant reduction in areas of infolding at the proximal edge 92 of the graft material 90, since strut coverage is provided around a significantly enhanced perimeter of the proximal edge 92 of the graft material 90.

As will be apparent, greater or fewer than 24 total different regions may be provided that are capable of preventing infolding at the proximal edge 92 of the graft material 90, in accordance with the teachings of the present invention. Moreover, the relative circumferential spacing between such regions may be varied, as the dimensions provided herein are for exemplary purposes. It should also be noted that the proximal apices 112 of the second stent 110 may axially overlap with portions of the first and second leg regions 70 and 80 of the stent 20, or the proximal apices 112 may be disposed slightly axially distal to the first and second leg regions 70, as generally depicted in FIG. 4.

Moreover, while one exemplary zig-zag stent 110 is shown as part of the stent-graft in FIG. 4, the stent-graft may have any number of stents having any variety of shapes, so long as the most proximal stent overlapping the graft material 90 embodies at least one region disposed in a position and manner similar to the proximal apices 112 of the exemplary stent 110.

Finally, it should be noted that the stent 20 may be used as part of a stent-graft, as generally described in FIG. 4, or alternatively may be used as a stand-alone stent to provide support to a vessel or duct without an attached graft material. In the latter embodiment, the stent 20 may be used to treat a wide range of conditions, including but not limited to arterial and biliary stenoses.

Referring to FIG. 5, a portion of a strut is similar to the stent 20 above, with the exception that an alternative distal transition region 50' comprises an enhanced width. In particular, a first outward taper 97 is provided between the first angled strut segment 57 and the distal transition region 50', and a second outward taper 98 is provided between the second angled strut segment 57 and the distal transition region 50'. By enhancing the width of the distal transition region 50', the structural integrity of the stent may be enhanced in this region, which may be advantageous given the provision of the slit 51 forming the integral barb 52, and the bifurcation into first and second leg regions 70 and 80.

Figure 6:
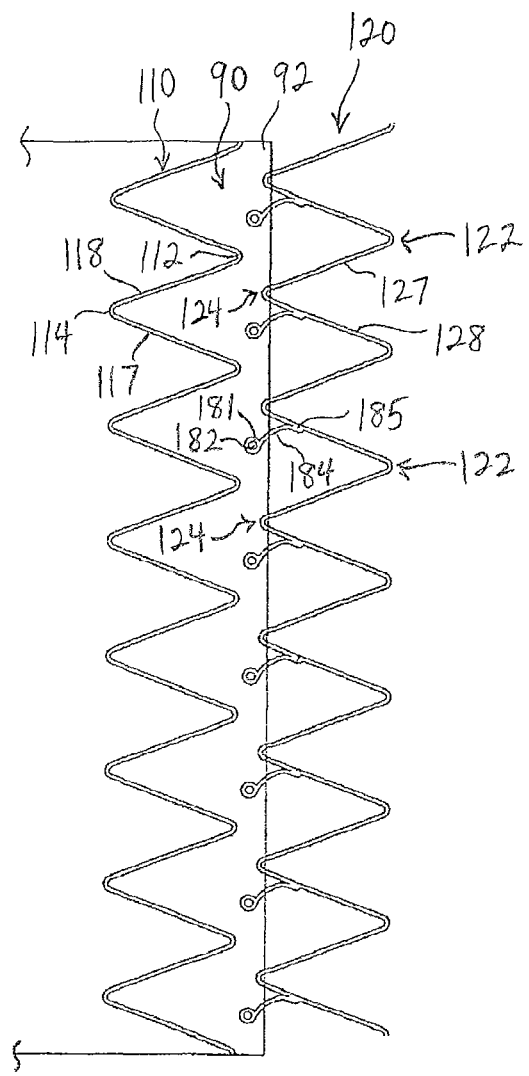
FIG. 6 is a side view depicting an alternative stent being coupled to a graft to form a stent-graft.

Referring to FIG. 6, an alternative stent 120 is coupled to a proximal edge 92 of the graft material 90 to form a stent-graft. The stent 120 comprises a generally zig-zag shape, and may be formed from a wire comprising a series of proximal apices 122 disposed at the proximal end of the stent 120, a series of distal apices 124 disposed at the distal end of the stent 120, and a plurality of first and second strut segments 127 and 128 disposed between the series of proximal apices 122 and the series of distal apices 124, as shown in FIG. 6. In this example, each of the second strut segments 128 comprises an extension region 184, which provides a similar function as the extension region 84 described above. Each extension region 184 comprises a proximal end that is secured to the angled strut segment 128 at a location 185 between the proximal and distal apices 122 and 124. The proximal end of the extension region 184 may be secured to the angled strut segment 128 at location 185 in a suitable manner, including but not limited to soldering, welding, mechanical attachment, friction fit, and the like. Further, the extension 184 comprises a distal end transitioning into a body region 181 having a suture bore 182, similar to the body region 81 and the suture bore 82 described above. Like the embodiment of FIGS. 1-4 above, in a compressed state, the body region 181 having the suture bore 182 may be positioned distally of an adjacent distal apex 124, and such axial spacing may reduce the delivery profile of the device.

Advantageously, in the deployed state shown in FIG. 6, a circumferential spacing is provided between the distal apices 124 and the body regions 181 of the extension regions 184. By providing a bifurcated distal apex having circumferentially spaced-apart regions 124 and 181, infolding at the proximal edge 92 of the graft material 90 may be reduced, in the manner described above with respect to FIGS. 1-4. Moreover, the principles described above with respect to FIGS. 1-4 regarding the degree of circumferential spacing $x_1$, $x_2$ and $x_3$, the angle $\alpha$ and the distance $L_1$ may be applied with respect to the embodiment of FIG. 6 to provide an optimal arrangement of components. In this manner, for the embodiment of FIG. 6, there is expected to be a significant reduction in areas of infolding at the proximal edge 92 of the graft material 90, since strut coverage is provided around an enhanced perimeter of the proximal edge 92 of the graft material 90.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A stent-graft, comprising:
a substantially tubular graft material; and
a stent coupled to the graft material, the stent having proximal and distal ends and further having compressed and deployed states, the proximal end being disposed proximally beyond a proximal edge of the graft material, and the distal end having at least one portion overlapping with the proximal edge of the graft material,
where the stent comprises at least one distal apex having a bifurcation extending into first and second leg regions, where a distal end of the first leg region is positioned to overlap the graft material at a location circumferentially spaced apart from a location at which a distal end of the second leg region overlaps the graft material in the deployed state,
wherein the first and second leg regions are separate and distinct, and only connect to the stent at the distal apex having the bifurcation from which they extend,
where the first leg region is generally parallel to a longitudinal axis of the stent in both the compressed and deployed states, and where the second leg region is parallel to the longitudinal axis in the compressed state but angled relative to the longitudinal axis in the deployed state.

2. The stent-graft of claim 1, where the distal end of the first leg region is coupled to the graft material at a location that is proximal to a location at which the distal end of the second leg region is coupled to the graft material in the compressed state.

3. The stent-graft of claim 1, where the first leg region comprises a suture bore and the second leg region also comprises a suture bore, where the graft material is secured to the stent at the suture bores of the first and second leg regions.

4. The stent-graft of claim 3, where the suture bore of the second leg region is positioned distally of the suture bore of the first leg region in the compressed state.

5. The stent-graft of claim 4, where the suture bore of the second leg region moves in a distal to proximal direction during deployment, such that the suture bore of the second leg region is approximately even with an axial position of the suture bore of the first leg region in the deployed state.

6. The stent-graft of claim 3, where the first leg region further comprises an imaging bore disposed proximal to the suture bore of the first leg region, the imaging bore being disposed at a location corresponding to an endpoint of the proximal edge of the graft material.

7. The stent-graft of claim 1, where the first leg region is oriented approximately parallel to the longitudinal axis of the stent in the deployed state, and where the second leg region is disposed at an angle of between about 15 and about 75 degrees relative to the first leg region in the deployed state.

8. The stent-graft of claim 1, where a second stent is provided at a location overlapping the graft material, the second stent having a proximal apex that is positioned circumferentially between the distal ends of the first and second leg regions in the deployed state.

9. A stent-graft, comprising:
a substantially tubular graft material;
a first stent coupled to the graft material, the first stent having proximal and distal ends and further having compressed and deployed states, the proximal end being disposed proximally beyond a proximal edge of the graft material, and the distal end having at least one portion overlapping with the proximal edge of the graft material,
where the first stent comprises at least one distal apex having a bifurcation extending into first and second leg regions, wherein the first and second leg regions are separate and distinct, and only connect to the first stent at the distal apex having the bifurcation from which they extend, and
a second stent disposed at a location overlapping the graft material, the second stent having a proximal apex that is positioned circumferentially between distal ends of the first and second leg regions in the deployed state,
where the first leg region is oriented approximately parallel to a longitudinal axis of the first stent in the deployed state, and where the second leg region is disposed at an angle of between about 15 and about 75 degrees relative to the first leg region in the deployed state.

10. The stent-graft of claim 9, where the distal end of the first leg region is coupled to the graft material at a location that is proximal to a location at which the distal end of the second leg region is coupled to the graft material in the compressed state.

11. The stent-graft of claim 9, where the first leg region is generally parallel to the longitudinal axis of the first stent in both the compressed and deployed states, and where the second leg region is parallel to the longitudinal axis in the compressed state but angled relative to the longitudinal axis in the deployed state.

12. The stent-graft of claim 9, where the first leg region comprises a suture bore and the second leg region also comprises a suture bore, where the graft material is secured to the first stent at the suture bores of the first and second leg regions.

13. The stent-graft of claim 12, where the suture bore of the second leg region is positioned distally of the suture bore of the first leg region in the compressed state.

14. The stent-graft of claim 13, where the suture bore of the second leg region moves in a distal to proximal direction during deployment, such that the suture bore of the second leg region is approximately even with an axial position of the suture bore of the first leg region in the deployed state.

15. A stent-graft, comprising:
a substantially tubular graft material; and
a first stent coupled to the graft material, the first stent comprising a generally zig-zag shape, and formed from a wire comprising a series of proximal apices disposed at a proximal end of the first stent, a series of distal apices disposed at a distal end of the first stent, and a plurality of first and second strut segments disposed between the series of proximal apices and the series of distal apices, where the proximal apices are disposed proximally beyond a proximal edge of the graft material, and the distal apices at least partially overlap with the proximal edge of the graft material; and an extension region extending from at least one strut segment, where the extension region comprises a proximal end that is secured to the at least one strut segment at a location between the proximal and distal apices, and where the extension region comprises a distal end that is circumferentially spaced apart from an adjacent distal apex in a deployed state, where the distal end of the extension region comprises a body region having a suture bore, where the extension region is secured to the graft material at the suture bore, and where the body region having the suture bore is positioned distally of the adjacent distal apex in a compressed state.

16. The stent-graft of claim 15, where a second stent is provided at a location overlapping the graft material, the second stent having a proximal apex that is positioned circumferentially between one of the distal apices of the first stent and the distal end of the extension region.

17. A stent-graft, comprising:

a substantially tubular graft material; and a stent coupled to the graft material, the stent having proximal and distal ends and further having compressed and deployed states, the proximal end being disposed proximally beyond a proximal edge of the graft material, and the distal end having at least one portion overlapping with the proximal edge of the graft material, where the stent comprises at least one distal apex having a bifurcation extending into first and second leg regions, where a distal end of the first leg region is positioned to overlap the graft material at a location circumferentially spaced apart from a location at which a distal end of the second leg region overlaps the graft material in the deployed state, wherein the first and second leg regions are separate and distinct, and only connect to the stent at the distal apex having the bifurcation from which they extend, and where the distal end of the first leg region is coupled to the graft material at a location that is proximal to a location at which the distal end of the second leg region is coupled to the graft material in the compressed state.

\* \* \* \* \*